United States Patent
Bressan et al.

(10) Patent No.: US 7,238,865 B2
(45) Date of Patent: Jul. 3, 2007

(54) **SOS1 GENE FROM *HALOPHILA* THAT CONFERS SALT TOLERANCE**

(75) Inventors: Ray A. Bressan, W. Lafayette, IN (US); Paul M. Hasegawa, Lafayette, IN (US)

(73) Assignee: Purdue Research Foundation, West LaFayette, IN (US)

( * ) Notice: Subject to any disclaimer, the term of this patent is extended or adjusted under 35 U.S.C. 154(b) by 0 days.

(21) Appl. No.: 11/274,081

(22) Filed: Nov. 14, 2005

(65) Prior Publication Data
US 2006/0117416 A1 Jun. 1, 2006

Related U.S. Application Data

(60) Provisional application No. 60/628,096, filed on Nov. 15, 2004.

(51) Int. Cl.
*A01H 5/00* (2006.01)
*C12N 15/82* (2006.01)
*C12N 15/29* (2006.01)

(52) U.S. Cl. .................. 800/295; 435/320.1; 435/419; 435/468; 800/312; 800/278; 536/23.6

(58) Field of Classification Search .................. None
See application file for complete search history.

(56) References Cited

U.S. PATENT DOCUMENTS

2002/0083485 A1* 6/2002 Zhu et al. .................. 800/278

OTHER PUBLICATIONS

Keskin et al. (Protein Science, 13:1043-1055, 2004).*
Thornton et al. (Nature structural Biology, structural genomics supplement, Nov. 2000).*
Guo et al. (PNAS, 101: 9205-9210, 2004).*
An et al. (NCBI, GenBank, Sequence Accession No. AY363875, Oct. 2003).*

* cited by examiner

*Primary Examiner*—David H. Kruse
*Assistant Examiner*—Vinod Kumar
(74) *Attorney, Agent, or Firm*—Bose McKinney & Evans LLP

(57) ABSTRACT

An SOS gene has been isolated through PCR cloning from *Thellungiella halophila* and is designated TSOS1. The polynucleotide encodes a transmembrane protein with similarities to plasma membrane $Na^+/H^+$ antiporters from bacteria and fungi. The invention encompasses the TSOS1 gene, the corresponding protein, closely related polypeptides that confer salt tolerance, and related polynucleotides that encode a polypeptide that has Na+/H+ antiporter activity.

12 Claims, No Drawings

SEQUENCE LISTING

<160> NUMBER OF SEQ ID NOS: 3

<210> SEQ ID NO 1
<211> LENGTH: 3442
<212> TYPE: DNA
<213> ORGANISM: Thellungiella halophila

<400> SEQUENCE: 1

```
atggcgactg taatcgaagc ggtgatgccg tataggcttc tggaggacga gaccggttcg     60
ccggaaggag aatctagccc cgttgacgcc gttctcttcg tcgggatgtc tctggtgctc    120
ggtatagctt ccgggcattt gcttcgcggg actagggttc cttacaccgt cgctctactc    180
gttatcggga ttgctcttgg atcgctcgaa tatggaaccc atcataacct tgggaagctc    240
```

-continued

```
ggccatggaa ttcgtatctg gaacgaaatc aaccctgaac ttcttttggc cgttttttctt    300
ccggctcttc ttttcgagag tgccttctcg atggaagttc accagatcaa gagatgtctg    360
ggacaaatgg tgctacttgc tgggcctgga gttctcattt caaccttttg tctggcatcg    420
cttgttaagc tcacgtttcc gtatgactgg gactggaaaa cgtcgttgtt gcttggggga    480
cttttaagtg ctactgatcc tgttgctgtt gttgctttgc ttaaagagct tggtgctagt    540
aagaagctaa gcacagtcat tgaaggggaa tccctgatga atgatgggac ggctattgtg    600
gttttccagt tattcttaaa gatggttatg ggtcatagtt ctggctggtc ttctataatc    660
acatttctga ttagagtcgc acttggagct gttggcattg gtatcgcttt tggcattgcc    720
tcggttcttt ggctcaagtt catattcaac gacacagtaa ttgagattac tcttacgatt    780
gcagtgagct acttcgcata ttacactgct caagagtggg ctgggcttc tggtgttttg    840
acggtgatga ctttgggcat gttttatgct gcatttgcaa gaacagcatt taaaggggac    900
agtcaaagaa gtttgcatca cttctgggaa atggtcgcat atattgcaaa actttgatt    960
tttatcctca gtggtgttgt cattgctgaa ggcattctcg acagcgataa gattgcgtac    1020
caagggagtt catggggata tcttttctcta ctatacttat acatccaact atcgcgttgt    1080
gttgttgttg gagttctgta ttcatttta tgtcgcgttg gctatggctt ggattggaaa    1140
gaagccatta tactcgtatg gtctggtttg aggggtgcag tggcgctctc actttcttta    1200
tccgtgaagc aatcaagcgg aaattcattt ctcagcaccg agacaggaac aatgtttatt    1260
ttcttcactg gtggaatcgt gttcctgact ctgatagtta atggatccac tacccaattt    1320
gctctgcgcc ttcttcgcat ggacggttta ccagcctcaa agatacgaat attggattat    1380
acaaagtatg aaatgctgaa taaggcctta caagcgtttg aagatctagg agacgatgaa    1440
gagttaggac ctgctgactg gcctacagtt gagagttata tttcgagctt aaaagattca    1500
gaaggggaac aagttcatcc tcatagtggc tctaagcctg aaatcttga ccatacgagt    1560
ttaaaggaca tacgtatacg tttcttaaat ggtgttcagg cagcttactg ggagatgctt    1620
gatgaaggaa gaatatctga aagtactgct aatattttga tgcggtcagt ggatgaggcg    1680
ttggatcata tttcgacgga gcctttatgt gactggagag gtctaaaatc gcatgttaag    1740
ttcccgggct actacaactt tcttcattct aagattatcc ctgggaagtt ggtcatatac    1800
tttgctgtcg atagactgga atctgcttgc tacatttccg ctgcatttct tcgcgcacat    1860
acaattgcac ggcagcaatt gtatgatttt cttggggaga gtaatatcgg ttctactgta    1920
atcaaggaaa gtgagaccga aggagaggag gcgaaagagt tcttggaaaa agtccgatct    1980
tcacttcctc aggttctccg tgttgtgaaa acaaaacaag taacttattc agtgctgagt    2040
catttactcg attacattca aaaccttgag aagattggct tgctggagga aaaagaaatc    2100
gctcatcttc atgatgctgt tcagactggc ttgaagaagc ttttgagaaa ccctccaata    2160
gtaaaacttc caaaattaag cgacctgatc acctcgcatc ctttatctgg tgcccttccg    2220
tctgcaatat gtgaacctct aaaacactcg aaaaaagaaa caatgaagct gcgtggtgtg    2280
acgctttata agaaggttc aaaccaact ggagtctggc taattttcga tggcattgtt    2340
aagtggaaaa gcaaaggctt aagcaacaat cactcgctgc atccaacatt ttctcatggt    2400
agtacactgg gactctacga agtcctcact gggaagccat atatgtgcga cgtgattaca    2460
gattctgtgg ttcttttgctt ttttatcaat agtgagagaa tactatctta tgtacaatcg    2520
gattccacca ttgaagattt cctttggaag gaaagtgcat tggtgcttct aaagctattg    2580
```

-continued

```
cgtcctcaaa catttgaaaa agtgccaatg catgaattaa gggcccttgt tccgctgaa    2640 agctcgaaac agacaacata tgtatctgga gaatcaattg aaatcgatca caacagcgtc   2700
ggtttgttat tagaaggatt cataaaagca gttggtatcc aagaagagct tcttatagca   2760
tctcctgctg cattattgca ttctaacgag aatcaaagct tccgtaattc atcagaagct   2820
tcgggtatcc tgagagtgag tttctcacga caagcagcac gatacagtgt ggagacaaga   2880
gcaagagtaa tcatcttcaa ccacggtgca tttggagctc ataggactct acaacgaaaa   2940
ccatcgacgt tagcatcacc acgtgccaca agctctgacc accagctcaa gagatcagct   3000
agcaaagaac acagaggtct catgagatgg cctgagaata tatacaaagc cgggcaagaa   3060
gaagagatga atggaaagac attaaacttg tctgaacgag cgatgcaact tagcattttc   3120
ggcagcacgg aaaatctgta caaaggagt gtaagtttcg gtgggctgaa caataacaag    3180
gcacaagata acttatcgta caagaaactc ccatcaacct cagctcaagg tcttttttca   3240
gcaaaatcgg aaggctcaat ggcaaccact aagcaggttg aaagccggaa atttgtgtct   3300
cagcttcctc cgttagctgc atctgcagaa ggcagctcga ggcgagaaac gatggcggaa   3360
gaatcaagcg atgatgaagg tgaaggaatc attgtgagga tcgattctcc gagtacgatc   3420
gttttcagga acgatctatg aa                                            3442
```

<210> SEQ ID NO 2
<211> LENGTH: 3442
<212> TYPE: DNA
<213> ORGANISM: Thellungiella halophila
<220> FEATURE:
<221> NAME/KEY: CDS
<222> LOCATION: (1)..(3441)

<400> SEQUENCE: 2

```
atg gcg act gta atc gaa gcg gtg atg ccg tat agg ctt ctg gag gac       48
Met Ala Thr Val Ile Glu Ala Val Met Pro Tyr Arg Leu Leu Glu Asp
1               5                   10                  15 gag acc ggt tcg ccg gaa gga gaa tct agc ccc gtt gac gcc gtt ctc       96
Glu Thr Gly Ser Pro Glu Gly Glu Ser Ser Pro Val Asp Ala Val Leu
                20                  25                  30 ttc gtc ggg atg tct ctg gtg ctc ggt ata gct tcc ggg cat ttg ctt      144
Phe Val Gly Met Ser Leu Val Leu Gly Ile Ala Ser Gly His Leu Leu
            35                  40                  45 cgc ggg act agg gtt cct tac acc gtc gct cta ctc gtt atc ggg att      192
Arg Gly Thr Arg Val Pro Tyr Thr Val Ala Leu Leu Val Ile Gly Ile
        50                  55                  60 gct ctt gga tcg ctc gaa tat gga acc cat cat aac ctt ggg aag ctc      240
Ala Leu Gly Ser Leu Glu Tyr Gly Thr His His Asn Leu Gly Lys Leu
65                  70                  75                  80 ggc cat gga att cgt atc tgg aac gaa atc aac cct gaa ctt ctt ttg      288
Gly His Gly Ile Arg Ile Trp Asn Glu Ile Asn Pro Glu Leu Leu Leu
                85                  90                  95 gcc gtt ttt ctt ccg gct ctt ctt ttc gag agt gcc ttc tcg atg gaa      336
Ala Val Phe Leu Pro Ala Leu Leu Phe Glu Ser Ala Phe Ser Met Glu
            100                 105                 110 gtt cac cag atc aag aga tgt ctg gga caa atg gtg cta ctt gct ggg      384
Val His Gln Ile Lys Arg Cys Leu Gly Gln Met Val Leu Leu Ala Gly
        115                 120                 125 cct gga gtt ctc att tca acc ttt tgt ctg gca tcg ctt gtt aag ctc      432
Pro Gly Val Leu Ile Ser Thr Phe Cys Leu Ala Ser Leu Val Lys Leu
    130                 135                 140 acg ttt ccg tat gac tgg gac tgg aaa acg tcg ttg ttg ctt ggg gga      480
Thr Phe Pro Tyr Asp Trp Asp Trp Lys Thr Ser Leu Leu Leu Gly Gly
```

```
                                                                            -continued
145             150             155             160 ctt tta agt gct act gat cct gtt gct gtt gtt gct ttg ctt aaa gag     528
Leu Leu Ser Ala Thr Asp Pro Val Ala Val Val Ala Leu Leu Lys Glu
            165             170             175 ctt ggt gct agt aag aag cta agc aca gtc att gaa ggg gaa tcc ctg     576
Leu Gly Ala Ser Lys Lys Leu Ser Thr Val Ile Glu Gly Glu Ser Leu
            180             185             190 atg aat gat ggg acg gct att gtg gtt ttc cag tta ttc tta aag atg     624
Met Asn Asp Gly Thr Ala Ile Val Val Phe Gln Leu Phe Leu Lys Met
            195             200             205 gtt atg ggt cat agt tct ggc tgg tct tct ata atc aca ttt ctg att     672
Val Met Gly His Ser Ser Gly Trp Ser Ser Ile Ile Thr Phe Leu Ile
            210             215             220 aga gtc gca ctt gga gct gtt ggc att ggt atc gct ttt ggc att gcc     720
Arg Val Ala Leu Gly Ala Val Gly Ile Gly Ile Ala Phe Gly Ile Ala
225             230             235             240 tcg gtt ctt tgg ctc aag ttc ata ttc aac gac aca gta att gag att     768
Ser Val Leu Trp Leu Lys Phe Ile Phe Asn Asp Thr Val Ile Glu Ile
            245             250             255 act ctt acg att gca gtg agc tac ttc gca tat tac act gct caa gag     816
Thr Leu Thr Ile Ala Val Ser Tyr Phe Ala Tyr Tyr Thr Ala Gln Glu
            260             265             270 tgg gct ggg gct tct ggt gtt ttg acg gtg atg act ttg ggc atg ttt     864
Trp Ala Gly Ala Ser Gly Val Leu Thr Val Met Thr Leu Gly Met Phe
            275             280             285 tat gct gca ttt gca aga aca gca ttt aaa ggg gac agt caa aga agt     912
Tyr Ala Ala Phe Ala Arg Thr Ala Phe Lys Gly Asp Ser Gln Arg Ser
            290             295             300 ttg cat cac ttc tgg gaa atg gtc gca tat att gca aat act ttg att     960
Leu His His Phe Trp Glu Met Val Ala Tyr Ile Ala Asn Thr Leu Ile
305             310             315             320 ttt atc ctc agt ggt gtt gtc att gct gaa ggc att ctc gac agc gat    1008
Phe Ile Leu Ser Gly Val Val Ile Ala Glu Gly Ile Leu Asp Ser Asp
            325             330             335 aag att gcg tac caa ggg agt tca tgg gga tat ctt ttt cta cta tac    1056
Lys Ile Ala Tyr Gln Gly Ser Ser Trp Gly Tyr Leu Phe Leu Leu Tyr
            340             345             350 tta tac atc caa cta tcg cgt tgt gtt gtt gtt gga gtt ctg tat tca    1104
Leu Tyr Ile Gln Leu Ser Arg Cys Val Val Val Gly Val Leu Tyr Ser
            355             360             365 ttt tta tgt cgc gtt ggc tat ggc ttg gat tgg aaa gaa gcc att ata    1152
Phe Leu Cys Arg Val Gly Tyr Gly Leu Asp Trp Lys Glu Ala Ile Ile
            370             375             380 ctc gta tgg tct ggt ttg agg ggt gca gtg gcg ctc tca ctt tct tta    1200
Leu Val Trp Ser Gly Leu Arg Gly Ala Val Ala Leu Ser Leu Ser Leu
385             390             395             400 tcc gtg aag caa tca agc gga aat tca ttt ctc agc acc gag aca gga    1248
Ser Val Lys Gln Ser Ser Gly Asn Ser Phe Leu Ser Thr Glu Thr Gly
            405             410             415 aca atg ttt att ttc ttc act ggt gga atc gtg ttc ctg act ctg ata    1296
Thr Met Phe Ile Phe Phe Thr Gly Gly Ile Val Phe Leu Thr Leu Ile
            420             425             430 gtt aat gga tcc act acc caa ttt gct ctg cgc ctt ctt cgc atg gac    1344
Val Asn Gly Ser Thr Thr Gln Phe Ala Leu Arg Leu Leu Arg Met Asp
            435             440             445 ggt tta cca gcc tca aag ata cga ata ttg gat tat aca aag tat gaa    1392
Gly Leu Pro Ala Ser Lys Ile Arg Ile Leu Asp Tyr Thr Lys Tyr Glu
450             455             460 atg ctg aat aag gcc tta caa gcg ttt gaa gat cta gga gac gat gaa    1440
```

|  |  | |
|---|---|---|
| Met Leu Asn Lys Ala Leu Gln Ala Phe Glu Asp Leu Gly Asp Asp Glu<br>465                              470                        475                        480 | |

```
gag tta gga cct gct gac tgg cct aca gtt gag agt tat att tcg agc      1488
Glu Leu Gly Pro Ala Asp Trp Pro Thr Val Glu Ser Tyr Ile Ser Ser
            485                 490                 495 tta aaa gat tca gaa ggg gaa caa gtt cat cct cat agt ggc tct aag      1536
Leu Lys Asp Ser Glu Gly Glu Gln Val His Pro His Ser Gly Ser Lys
        500                 505                 510 cct gga aat ctt gac cat acg agt tta aag gac ata cgt ata cgt ttc      1584
Pro Gly Asn Leu Asp His Thr Ser Leu Lys Asp Ile Arg Ile Arg Phe
    515                 520                 525 tta aat ggt gtt cag gca gct tac tgg gag atg ctt gat gaa gga aga      1632
Leu Asn Gly Val Gln Ala Ala Tyr Trp Glu Met Leu Asp Glu Gly Arg
530                 535                 540 ata tct gaa agt act gct aat att ttg atg cgg tca gtg gat gag gcg      1680
Ile Ser Glu Ser Thr Ala Asn Ile Leu Met Arg Ser Val Asp Glu Ala
545                 550                 555                 560 ttg gat cat att tcg acg gag cct tta tgt gac tgg aga ggt cta aaa      1728
Leu Asp His Ile Ser Thr Glu Pro Leu Cys Asp Trp Arg Gly Leu Lys
                565                 570                 575 tcg cat gtt aag ttc ccg ggc tac tac aac ttt ctt cat tct aag att      1776
Ser His Val Lys Phe Pro Gly Tyr Tyr Asn Phe Leu His Ser Lys Ile
            580                 585                 590 atc cct ggg aag ttg gtc ata tac ttt gct gtc gat aga ctg gaa tct      1824
Ile Pro Gly Lys Leu Val Ile Tyr Phe Ala Val Asp Arg Leu Glu Ser
        595                 600                 605 gct tgc tac att tcc gct gca ttt ctt cgc gca cat aca att gca cgg      1872
Ala Cys Tyr Ile Ser Ala Ala Phe Leu Arg Ala His Thr Ile Ala Arg
    610                 615                 620 cag caa ttg tat gat ttt ctt ggg gag agt aat atc ggt tct act gta      1920
Gln Gln Leu Tyr Asp Phe Leu Gly Glu Ser Asn Ile Gly Ser Thr Val
625                 630                 635                 640 atc aag gaa agt gag acc gaa gga gag gag gcg aaa gag ttc ttg gaa      1968
Ile Lys Glu Ser Glu Thr Glu Gly Glu Glu Ala Lys Glu Phe Leu Glu
                645                 650                 655 aaa gtc cga tct tca ctt cct cag gtt ctc cgt gtt gtg aaa aca aaa      2016
Lys Val Arg Ser Ser Leu Pro Gln Val Leu Arg Val Val Lys Thr Lys
            660                 665                 670 caa gta act tat tca gtg ctg agt cat tta ctc gat tac att caa aac      2064
Gln Val Thr Tyr Ser Val Leu Ser His Leu Leu Asp Tyr Ile Gln Asn
        675                 680                 685 ctt gag aag att ggc ttg ctg gag gaa aaa gaa atc gct cat ctt cat      2112
Leu Glu Lys Ile Gly Leu Leu Glu Glu Lys Glu Ile Ala His Leu His
    690                 695                 700 gat gct gtt cag act ggc ttg aag aag ctt ttg aga aac cct cca ata      2160
Asp Ala Val Gln Thr Gly Leu Lys Lys Leu Leu Arg Asn Pro Pro Ile
705                 710                 715                 720 gta aaa ctt cca aaa tta agc gac ctg atc acc tcg cat cct tta tct      2208
Val Lys Leu Pro Lys Leu Ser Asp Leu Ile Thr Ser His Pro Leu Ser
                725                 730                 735 ggt gcc ctt ccg tct gca ata tgt gaa cct cta aaa cac tcg aaa aaa      2256
Gly Ala Leu Pro Ser Ala Ile Cys Glu Pro Leu Lys His Ser Lys Lys
            740                 745                 750 gaa aca atg aag ctg cgt ggt gtg acg ctt tat aaa gaa ggt tca aaa      2304
Glu Thr Met Lys Leu Arg Gly Val Thr Leu Tyr Lys Glu Gly Ser Lys
        755                 760                 765 cca act gga gtc tgg cta att ttc gat ggc att gtt aag tgg aaa agc      2352
Pro Thr Gly Val Trp Leu Ile Phe Asp Gly Ile Val Lys Trp Lys Ser
    770                 775                 780
```

```
aaa ggc tta agc aac aat cac tcg ctg cat cca aca ttt tct cat ggt          2400
Lys Gly Leu Ser Asn Asn His Ser Leu His Pro Thr Phe Ser His Gly
785                 790                 795                 800 agt aca ctg gga ctc tac gaa gtc ctc act ggg aag cca tat atg tgc          2448
Ser Thr Leu Gly Leu Tyr Glu Val Leu Thr Gly Lys Pro Tyr Met Cys
                805                 810                 815 gac gtg att aca gat tct gtg gtt ctt tgc ttt ttt atc aat agt gag          2496
Asp Val Ile Thr Asp Ser Val Val Leu Cys Phe Phe Ile Asn Ser Glu
            820                 825                 830 aga ata cta tct tat gta caa tcg gat tcc acc att gaa gat ttc ctt          2544
Arg Ile Leu Ser Tyr Val Gln Ser Asp Ser Thr Ile Glu Asp Phe Leu
        835                 840                 845 tgg aag gaa agt gca ttg gtg ctt cta aag cta ttg cgt cct caa aca          2592
Trp Lys Glu Ser Ala Leu Val Leu Leu Lys Leu Leu Arg Pro Gln Thr
850                 855                 860 ttt gaa aaa gtg cca atg cat gaa tta agg gcc ctt gtt tcc gct gaa          2640
Phe Glu Lys Val Pro Met His Glu Leu Arg Ala Leu Val Ser Ala Glu
865                 870                 875                 880 agc tcg aaa cag aca aca tat gta tct gga gaa tca att gaa atc gat          2688
Ser Ser Lys Gln Thr Thr Tyr Val Ser Gly Glu Ser Ile Glu Ile Asp
                885                 890                 895 cac aac agc gtc ggt ttg tta tta gaa gga ttc ata aaa gca gtt ggt          2736
His Asn Ser Val Gly Leu Leu Leu Glu Gly Phe Ile Lys Ala Val Gly
            900                 905                 910 atc caa gaa gag ctt ctt ata gca tct cct gct gca tta ttg cat tct          2784
Ile Gln Glu Glu Leu Leu Ile Ala Ser Pro Ala Ala Leu Leu His Ser
        915                 920                 925 aac gag aat caa agc ttc cgt aat tca tca gaa gct tcg ggt atc ctg          2832
Asn Glu Asn Gln Ser Phe Arg Asn Ser Ser Glu Ala Ser Gly Ile Leu
930                 935                 940 aga gtg agt ttc tca cga caa gca gca cga tac agt gtg gag aca aga          2880
Arg Val Ser Phe Ser Arg Gln Ala Ala Arg Tyr Ser Val Glu Thr Arg
945                 950                 955                 960 gca aga gta atc atc ttc aac cac ggt gca ttt gga gct cat agg act          2928
Ala Arg Val Ile Ile Phe Asn His Gly Ala Phe Gly Ala His Arg Thr
                965                 970                 975 cta caa cga aaa cca tcg acg tta gca tca cca cgt gcc aca agc tct          2976
Leu Gln Arg Lys Pro Ser Thr Leu Ala Ser Pro Arg Ala Thr Ser Ser
            980                 985                 990 gac cac cag ctc aag aga tca gct agc aaa gaa cac aga ggt ctc atg          3024
Asp His Gln Leu Lys Arg Ser Ala Ser Lys Glu His Arg Gly Leu Met
        995                 1000                1005 aga tgg cct gag aat ata tac aaa gcc ggg caa gaa gaa gag atg             3069
Arg Trp Pro Glu Asn Ile Tyr Lys Ala Gly Gln Glu Glu Glu Met
1010                1015                    1020 aat gga aag aca tta aac ttg tct gaa cga gcg atg caa ctt agc             3114
Asn Gly Lys Thr Leu Asn Leu Ser Glu Arg Ala Met Gln Leu Ser
1025                1030                    1035 att ttc ggc agc acg gaa aat ctg tac aaa agg agt gta agt ttc             3159
Ile Phe Gly Ser Thr Glu Asn Leu Tyr Lys Arg Ser Val Ser Phe
    1040                1045                1050 ggt ggg ctg aac aat aac aag gca caa gat aac tta tcg tac aag             3204
Gly Gly Leu Asn Asn Asn Lys Ala Gln Asp Asn Leu Ser Tyr Lys
    1055                1060                1065 aaa ctc cca tca acc tca gct caa ggt ctt ttt tca gca aaa tcg             3249
Lys Leu Pro Ser Thr Ser Ala Gln Gly Leu Phe Ser Ala Lys Ser
    1070                1075                1080 gaa ggc tca atg gca acc act aag cag gtt gaa agc cgg aaa ttt             3294
Glu Gly Ser Met Ala Thr Thr Lys Gln Val Glu Ser Arg Lys Phe
    1085                1090                1095
```

```
gtg tct cag ctt cct ccg tta gct gca tct gca gaa ggc agc tcg      3339
Val Ser Gln Leu Pro Pro Leu Ala Ala Ser Ala Glu Gly Ser Ser
1100               1105                1110 agg cga gaa acg atg gcg gaa gaa tca agc gat gat gaa ggt gaa      3384
Arg Arg Glu Thr Met Ala Glu Glu Ser Ser Asp Asp Glu Gly Glu
1115               1120                1125 gga atc att gtg agg atc gat tct ccg agt acg atc gtt ttc agg      3429
Gly Ile Ile Val Arg Ile Asp Ser Pro Ser Thr Ile Val Phe Arg
1130               1135                1140 aac gat cta tga a                                                 3442
Asn Asp Leu
1145

<210> SEQ ID NO 3
<211> LENGTH: 1146
<212> TYPE: PRT
<213> ORGANISM: Thellungiella halophila

<400> SEQUENCE: 3

Met Ala Thr Val Ile Glu Ala Val Met Pro Tyr Arg Leu Leu Glu Asp
1               5                   10                  15

Glu Thr Gly Ser Pro Glu Gly Glu Ser Ser Pro Val Asp Ala Val Leu
            20                  25                  30

Phe Val Gly Met Ser Leu Val Leu Gly Ile Ala Ser Gly His Leu Leu
        35                  40                  45

Arg Gly Thr Arg Val Pro Tyr Thr Val Ala Leu Leu Val Ile Gly Ile
    50                  55                  60

Ala Leu Gly Ser Leu Glu Tyr Gly Thr His His Asn Leu Gly Lys Leu
65                  70                  75                  80

Gly His Gly Ile Arg Ile Trp Asn Glu Ile Asn Pro Glu Leu Leu Leu
                85                  90                  95

Ala Val Phe Leu Pro Ala Leu Leu Phe Glu Ser Ala Phe Ser Met Glu
            100                 105                 110

Val His Gln Ile Lys Arg Cys Leu Gly Gln Met Val Leu Leu Ala Gly
        115                 120                 125

Pro Gly Val Leu Ile Ser Thr Phe Cys Leu Ala Ser Leu Val Lys Leu
    130                 135                 140

Thr Phe Pro Tyr Asp Trp Asp Trp Lys Thr Ser Leu Leu Leu Gly Gly
145                 150                 155                 160

Leu Leu Ser Ala Thr Asp Pro Val Ala Val Val Ala Leu Leu Lys Glu
                165                 170                 175

Leu Gly Ala Ser Lys Lys Leu Ser Thr Val Ile Glu Gly Glu Ser Leu
            180                 185                 190

Met Asn Asp Gly Thr Ala Ile Val Val Phe Gln Leu Phe Leu Lys Met
        195                 200                 205

Val Met Gly His Ser Ser Gly Trp Ser Ser Ile Ile Thr Phe Leu Ile
    210                 215                 220

Arg Val Ala Leu Gly Ala Val Gly Ile Gly Ile Ala Phe Gly Ile Ala
225                 230                 235                 240

Ser Val Leu Trp Leu Lys Phe Ile Phe Asn Asp Thr Val Ile Glu Ile
                245                 250                 255

Thr Leu Thr Ile Ala Val Ser Tyr Phe Ala Tyr Tyr Thr Ala Gln Glu
            260                 265                 270

Trp Ala Gly Ala Ser Gly Val Leu Thr Val Met Thr Leu Gly Met Phe
        275                 280                 285
```

```
Tyr Ala Ala Phe Ala Arg Thr Ala Phe Lys Gly Asp Ser Gln Arg Ser
    290                 295                 300

Leu His His Phe Trp Glu Met Val Ala Tyr Ile Ala Asn Thr Leu Ile
305                 310                 315                 320

Phe Ile Leu Ser Gly Val Val Ile Ala Glu Gly Ile Leu Asp Ser Asp
                325                 330                 335

Lys Ile Ala Tyr Gln Gly Ser Ser Trp Gly Tyr Leu Phe Leu Leu Tyr
            340                 345                 350

Leu Tyr Ile Gln Leu Ser Arg Cys Val Val Gly Val Leu Tyr Ser
        355                 360                 365

Phe Leu Cys Arg Val Gly Tyr Gly Leu Asp Trp Lys Glu Ala Ile Ile
370                 375                 380

Leu Val Trp Ser Gly Leu Arg Gly Ala Val Ala Leu Ser Leu Ser Leu
385                 390                 395                 400

Ser Val Lys Gln Ser Ser Gly Asn Ser Phe Leu Ser Thr Glu Thr Gly
                405                 410                 415

Thr Met Phe Ile Phe Phe Thr Gly Gly Ile Val Phe Leu Thr Leu Ile
                420                 425                 430

Val Asn Gly Ser Thr Thr Gln Phe Ala Leu Arg Leu Leu Arg Met Asp
            435                 440                 445

Gly Leu Pro Ala Ser Lys Ile Arg Ile Leu Asp Tyr Thr Lys Tyr Glu
450                 455                 460

Met Leu Asn Lys Ala Leu Gln Ala Phe Glu Asp Leu Gly Asp Asp Glu
465                 470                 475                 480

Glu Leu Gly Pro Ala Asp Trp Pro Thr Val Glu Ser Tyr Ile Ser Ser
                485                 490                 495

Leu Lys Asp Ser Glu Gly Glu Gln Val His Pro His Ser Gly Ser Lys
            500                 505                 510

Pro Gly Asn Leu Asp His Thr Ser Leu Lys Asp Ile Arg Ile Arg Phe
        515                 520                 525

Leu Asn Gly Val Gln Ala Ala Tyr Trp Glu Met Leu Asp Glu Gly Arg
530                 535                 540

Ile Ser Glu Ser Thr Ala Asn Ile Leu Met Arg Ser Val Asp Glu Ala
545                 550                 555                 560

Leu Asp His Ile Ser Thr Glu Pro Leu Cys Asp Trp Arg Gly Leu Lys
                565                 570                 575

Ser His Val Lys Phe Pro Gly Tyr Tyr Asn Phe Leu His Ser Lys Ile
            580                 585                 590

Ile Pro Gly Lys Leu Val Ile Tyr Phe Ala Val Asp Arg Leu Glu Ser
        595                 600                 605

Ala Cys Tyr Ile Ser Ala Ala Phe Leu Arg Ala His Thr Ile Ala Arg
    610                 615                 620

Gln Gln Leu Tyr Asp Phe Leu Gly Glu Ser Asn Ile Gly Ser Thr Val
625                 630                 635                 640

Ile Lys Glu Ser Glu Thr Glu Gly Glu Glu Ala Lys Glu Phe Leu Glu
                645                 650                 655

Lys Val Arg Ser Ser Leu Pro Gln Val Leu Arg Val Val Lys Thr Lys
            660                 665                 670

Gln Val Thr Tyr Ser Val Leu Ser His Leu Leu Asp Tyr Ile Gln Asn
        675                 680                 685

Leu Glu Lys Ile Gly Leu Leu Glu Glu Lys Glu Ile Ala His Leu His
    690                 695                 700

Asp Ala Val Gln Thr Gly Leu Lys Lys Leu Leu Arg Asn Pro Pro Ile
```

-continued

```
            705                 710                 715                 720
Val Lys Leu Pro Lys Leu Ser Asp Leu Ile Thr Ser His Pro Leu Ser
                725                 730                 735
Gly Ala Leu Pro Ser Ala Ile Cys Glu Pro Leu Lys His Ser Lys Lys
                740                 745                 750
Glu Thr Met Lys Leu Arg Gly Val Thr Leu Tyr Lys Glu Gly Ser Lys
                755                 760                 765
Pro Thr Gly Val Trp Leu Ile Phe Asp Gly Ile Val Lys Trp Lys Ser
                770                 775                 780
Lys Gly Leu Ser Asn Asn His Ser Leu His Pro Thr Phe Ser His Gly
785                 790                 795                 800
Ser Thr Leu Gly Leu Tyr Glu Val Leu Thr Gly Lys Pro Tyr Met Cys
                805                 810                 815
Asp Val Ile Thr Asp Ser Val Val Leu Cys Phe Phe Ile Asn Ser Glu
                820                 825                 830
Arg Ile Leu Ser Tyr Val Gln Ser Asp Ser Thr Ile Glu Asp Phe Leu
                835                 840                 845
Trp Lys Glu Ser Ala Leu Val Leu Leu Lys Leu Leu Arg Pro Gln Thr
850                 855                 860
Phe Glu Lys Val Pro Met His Glu Leu Arg Ala Leu Val Ser Ala Glu
865                 870                 875                 880
Ser Ser Lys Gln Thr Thr Tyr Val Ser Gly Glu Ser Ile Glu Ile Asp
                885                 890                 895
His Asn Ser Val Gly Leu Leu Leu Glu Gly Phe Ile Lys Ala Val Gly
                900                 905                 910
Ile Gln Glu Glu Leu Leu Ile Ala Ser Pro Ala Ala Leu Leu His Ser
                915                 920                 925
Asn Glu Asn Gln Ser Phe Arg Asn Ser Ser Glu Ala Ser Gly Ile Leu
930                 935                 940
Arg Val Ser Phe Ser Arg Gln Ala Ala Arg Tyr Ser Val Glu Thr Arg
945                 950                 955                 960
Ala Arg Val Ile Ile Phe Asn His Gly Ala Phe Gly Ala His Arg Thr
                965                 970                 975
Leu Gln Arg Lys Pro Ser Thr Leu Ala Ser Pro Arg Ala Thr Ser Ser
                980                 985                 990
Asp His Gln Leu Lys Arg Ser Ala  Ser Lys Glu His Arg  Gly Leu Met
                995                 1000                1005
Arg Trp  Pro Glu Asn Ile Tyr  Lys Ala Gly Gln Glu  Glu Glu Met
     1010                1015                1020
Asn Gly  Lys Thr Leu Asn Leu  Ser Glu Arg Ala Met  Gln Leu Ser
     1025                1030                1035
Ile Phe  Gly Ser Thr Glu Asn  Leu Tyr Lys Arg Ser  Val Ser Phe
     1040                1045                1050
Gly Gly  Leu Asn Asn Asn Lys  Ala Gln Asp Asn Leu  Ser Tyr Lys
     1055                1060                1065
Lys Leu  Pro Ser Thr Ser Ala  Gln Gly Leu Phe Ser  Ala Lys Ser
     1070                1075                1080
Glu Gly  Ser Met Ala Thr Thr  Lys Gln Val Glu Ser  Arg Lys Phe
     1085                1090                1095
Val Ser  Gln Leu Pro Pro Leu  Ala Ala Ser Ala Glu  Gly Ser Ser
     1100                1105                1110
Arg Arg  Glu Thr Met Ala Glu  Glu Ser Ser Asp Asp  Glu Gly Glu
     1115                1120                1125
```

```
-continued

Gly Ile Ile Val Arg Ile Asp Ser Pro Ser Thr Ile Val Phe Arg
    1130        1135                1140

Asn Asp Leu
    1145
```

SOS1 GENE FROM *HALOPHILA* THAT CONFERS SALT TOLERANCE

CROSS-REFERENCE TO RELATED APPLICATIONS

The subject application claims the benefit of priority to U.S. Ser. No. 60/628,096, filed on Nov. 15, 2004, which is incorporated herein in its entirety.

FILED OF THE INVENTION

The present invention relates to proteins and nucleic acids that provide to salt tolerance in plants, and in particular the TSOS1 gene from *Thellungiella halophila*.

BACKGROUND OF THE INVENTION

High concentrations of saline in soils inhibit plant growth and further inhibit agricultural productivity. Modem agricultural practices including irrigation are known to increase salt concentrations when the available irrigation water evaporates, leaving dissolved salts behind. In areas containing salty soils such as Southern California, Arizona, New Mexico and Texas, it has become particularly important to develop salt tolerant cultivars of agronomically important crops. Salty soils decrease the rate at which water will enter the roots due to the osmotic pressure of the solution. If the salt concentrations are sufficiently high, water will actually be withdrawn from the plant roots, eventually leading to plant death.

Thus, development of salt tolerant cultivars is required to offset effects of irrigation, and for utilization of marginal agricultural areas, and use saltier irrigation water.

Traditional plant breeding methods require long term selection and testing to identify new cultivars. Thus far, these methods have not yielded crop plants cultivars with substantially improved salt tolerance.

Excessive sodium ions ($Na^+$) are toxic to plants because of adverse effects on cellular metabolism and ion homeostasis. Sodium ions in saline soils are toxic to plants due to their adverse effects on $K+/Na+$ homeostasis, cytosolic enzyme activities, photosynthesis and metabolism (Niu, et al. (1995) Plant Physiol. 109:735-742; Jacoby B. (1999) in Handbook of Plant and Crop Stress, ed. Pessarakli M (Marcel Dekker, NY), pp. 97-123)). Niu et al. (1995), supra, report three mechanisms that prevent accumulation of Na+ in the cytoplasm: restricted Na+ influx; active Na+ efflux and compartmentalization of Na+ in the vacuole. One example of restricted Na+ influx includes the wheat low affinity cation transporter LCT1 which may mediate Na+ influx into plant cells (Schachtman et al. (1997) PNAS 94:11079-84)). Another restriction on Na+ influx includes wheat high-affinity K+ transporter HKT1 which functions as a Na+-K+ co-transporter, which confers low-affinity Na+ uptake at toxic Na+ concentrations (Rubio et al. (1995) Science 270:1660-1663). Also, non-selective cation channels have been found to play important roles in mediating Na+ entry into plants (Amtmann et al. (1998) Adv. Bot. Res. 29:76-112)).

An example of Na+ compartmentalization in the vacuole includes the *Arabidopsis thaliana* ATNHX1 gene which encodes a tonoplast Na+/H+ antiporter (Gaxiola et al. (1999) PNAS 96:1480-85)).

Active Na+ efflux transporters have been found in fungi. In the yeast *Saccharomyces cerevisiae*, plasma membrane Na+-ATPases play a predominant role in Na+ efflux and salt tolerance (Haro et al. (1991) FEBS Lett. 291:189-191)). In the fungus *Schizosaccharomyces pombe*, Na+/H+ antiporters are more important for Na+ efflux and salt tolerance (Jia et al. (1992) EMBO J 11:1631-40)).

*Arabidopsis* is a glycophyte that is not very salt tolerant, but can adapt to elevated salt concentrations. Several *Arabidopsis* SOS mutants defective in salt tolerance have been characterized (Wu et al. (1996) Plant Cell 8:617-27; Liu et al. (1997) PNAS 94:14960-64; and Zhu et al. (1998) Plant Cell 10:1181-1191)). The SOS mutants are hypersensitive to high external Na+ or Li+ and also are unable to grow under very low external K+ concentrations (Zhu et al., (1998), supra)). The SOS mutants are defined as three loci, SOS1, SOS2 and SOS3 (Zhu et al. (1998), supra)). The SOS3 gene has homology to animal neuronal calcium sensors and the yeast calcineurin B subunit (Liu et al. (1998) Science 280:1943-45)). In yeast, mutations in calcineurin B lead to increased sensitivity of yeast cells to Na+ and Li+ concentration (Mendoza et al. (1994) J. Biol. Chem. 269:8792-96)). The SOS2 gene encodes a serine/threonine type protein kinase (Liu et al. (2000), PNAS, in press). Halfter et al. (2000) PNAS, in press, report that the SOS2 protein physically interacts with and is activated by SOS3, suggesting an SOS2/SOS3 regulatory pathway for Na+ and K+ homeostasis and salt tolerance in plants.

The SOS1 mutant is more sensitive to Na+ and Li+ stresses than the SOS2 and SOS3 mutant plants (Zhu et al. (1998), supra)). Double mutant analysis indicates that SOS1 functions in the same pathway as SOS2 and SOS3 (Liu et al. (1997), supra; and Zhu et al. (1998), supra)). The SOS1 protein may be a target for regulation by the SOS3/SOS2 pathway. The SOS1 gene has been cloned from *Arabidopsis thaliana* (U.S. Pat. No. 6,727,408). The SOS1 protein has Na+/H+ transporter activity and homology to Na+/H+ antiporters from bacteria and fungi. SOS1 transcript is up-regulated by NaCl stress. The SOS2 mutation abolishes SOS1 up-regulation in the shoot. In the SOS3 mutant, no SOS1 up-regulation is found in the shoot or root. SOS1 gene expression appears therefore to be regulated under NaCl stress by the SOS3/SOS2 regulatory pathway. (U.S. Pat. No. 6,727,408).

The salt cress, or *Thellungiella halophila*, can withstand dramatic salinity up to 500 mM NaCl and grow in salt far in excess of the capability of *Arabidopsis*. Salt cress has been suggested to be a favorable model for further study of salt tolerance because it has desirable life history traits (small size, short life cycle, self-pollination and high seed number), and favorable genetic traits (self-fertilization, a small genome, efficient transformation and mutagenesis). The salt cress genome is less than twice the size of *Arabidopsis*. EST analysis of hundreds of salt cress clones indicates 90-95% identities between *Arabidopsis* and salt cress cDNAs and amino acid sequences (Bressan et al. (2001) Plant Physiol. 127:1354).

A full-length cDNA microarray of *Arabidopsis* containing thousands of cDNAs including SOS1, has been used for expression profiling of salt cress genes. It was found that 6 genes were strongly induced in salt cress in response to high salinity stress, whereas 40 genes were identified as salt stress-inducible in *Arabidopsis*. The expression profiles of genes highly expressed in salt cress under normal growth conditions (not high salinity) were reported to resemble those *Arabidopsis* genes induced under abiotic stress (such as high salinity). It was suggested that salt cress constitutively overexpresses a large number of genes, including SOS1, even under unstressed conditions (Taji et al. (July 2004) Plant Physiol. 135:1697). Although Taji et al. report that an SOS1 gene is expressed in salt cress, they do not provide the sequence or report whether the salt cress SOS1 gene confers salt tolerance to salt cress.

Inan et al. (July 2004) Plant Physiol. 135:1718, report that the salt cress SOS1 gene is 84% homologous to the *Arabidopsis* SOS1 gene. This level of homology is less than the 90-95% homology observed between *Arabidopsis* and salt cress housekeeping genes.

SUMMARY OF THE INVENTION

An SOS gene has been isolated through PCR cloning from *Thellungiella halophila* and is designated TSOS1. The gene or polynucleotide encodes a transmembrane protein with similarities to plasma membrane $Na^+/H^+$ antiporters from bacteria and fungi. Existence of the predicted protein in *Thellungiella halophila* suggests that a plasma membrane-type $Na^+/H^+$ antiporter is generally essential for plant salt tolerance.

The isolated *Thellungiella* polynucleotide of SEQ ID NO: 1 encodes the contiguous amino acid sequence of SEQ ID NO: 3 that is a protein that effects $Na^+/H^+$ transporter activity.

In its various embodiments, the invention comprises:
(i) the polynucleotide of SEQ ID NO: 1;
(ii) a polynucleotide sequence having at least 85% homology to SEQ ID NO:1, wherein the homologous sequence encodes a polypeptide that has Na+/H+ transporter activity;
(iii) a polynucleotide sequence encoding the polypeptide of SEQ ID NO: 3, or encoding a homologous polypeptide having at least 84% homology to the polypeptide of SEQ ID NO: 3 and which has Na+/H+ transporter activity;
(iv) a polynucleotide having a sequence that has at least 85% homology to the sequence of (iii), and which encodes a polypeptide that has Na+/H+ transporter activity;
(v) a polynucleotide sequence that is a fragment of any of the sequences in (i)-(iv), wherein the fragment is at least 300 nucleotides in length, and wherein the fragment encodes a polypeptide that has Na+/H+ transporter activity; and
(vi) nucleic acid sequences complementary to or which hybridize under stringent conditions to any of the sequences of (i)-(v).

Regarding polynucleotide sequences described above under (ii), alternate embodiments include, with increasing preference, homologous polynucleotide sequences with minimum homology increasing incrementally by 1%, i.e., 86%, 87%, 88%, etc., up to and including 99%. Regarding the homologous polypeptide sequences described under (iii) above, alternate embodiments include, with increasing preference, homologous polypeptide sequences with minimum homology increasing incrementally by 1%, i.e., 85%, 86%, 87%, etc., up to and including 99%.

Regarding the polynucleotide fragment of (v) above, alternate embodiments include, with increasing preference, fragments with minimum lengths of 600, 900, 1200, 1500, 1800, 22100, 2400, 2700, 3000, 3300 nucleotides.

The invention also comprises a cassette comprising a heterologous promoter linked to any of the foregoing polynucleotides. In particular, the promoter can be an inducible promoter. The invention also comprises a vector which includes the cassette of heterologous promoter and foregoing polynucleotides.

Also included in the invention are host cells, including plant cells that comprise any of the foregoing polynucleotides, and transgenic plants comprising the foregoing polynucleotides. The transgenic plants can include crops, ornamentals, and trees, monocots and dicots. More specifically, this includes, without limitation, *Arabidopsis thaliana*, wheat, corn, peanut, cotton, oat, tomato, rice and soybean plants.

In another embodiment, the subject invention also comprises a method of making a transgenic plant with increased salt tolerance as compared to the plant's untransformed state. The transgenic plant is made by introducing any of the foregoing polynucleotides into the plant using methods known in the art.

The invention also includes the following polypeptides:
(i) the polypeptide of SEQ ID NO: 3;
(ii) a polypeptide with a sequence having at least 84% homology to SEQ ID NO: 3, and with increasing preference, homologous polypeptide sequences with minimum homology increasing incrementally by 1%, i.e., 85%, 86%, 87%, etc., up to and including 99%; wherein the homologous polypeptide has Na+/H+ transporter activity;
(iii) fragments of (i) or (ii), wherein said fragment is at least 100 amino acids in length, and with increasing preference, has a minimum length of 200, 300, 400, 500, 600, 700, 800, 900, 1000 and 1100 amino acids, and has Na+/H+ transporter activity.

The invention further comprises a method of identifying polynucleotides which encode a protein having Na+/H+ transporter activity, comprising: (a) identifying a polynucleotide in a nucleic acid sample or in a database that: (i) has at least 85% homology to SEQ ID NO: 1; (ii) has at least 85% homology to a polynucleotide that encodes SEQ ID NO.:3, or (iii) encodes a homologous polypeptide with at least 84% homology to SEQ ID NO: 3; (b) expressing the polynucleotide of (a) in a cell or transgenic plant; and (c) determining whether the cell or plant with the expressed polypeptide has Na+/H+ transporter activity. The polynucleotide that is identified can be substantially full-length relative to SEQ ID NO: 1, or a fragment that is at least 300 nucleotides in length. The identified fragment, with increasing preference, has a minimum length of 600, 900, 1200, 1500, 1800, 2100, 2400, 2700, 3000 or 3300 nucleotides.

The invention also comprises a method of identifying homologous or orthologous SOS1 polynucleotides in plants that are wild relatives of domesticated plant species. Such wild relatives are compatible with the domesticated crop species and are known to skilled artisans. The following table, table 1, taken from Colorado State University's Life Sciences Transgenic Crop program, sets forth compatible wild relatives. Wild relatives are generally considered to be more stress (cold, salt, etc.) tolerant. Those wild relatives in the table with an asterisk have been specifically reported to be more salt tolerant than their crop plants (see Wei et al. (2001) Plant Physiol. 125:1429 in relation to wheatgrass; and Latha et al. (2004) Annals of App. Biol. 144(2):177 in relation to breeding for salt tolerance).

TABLE 1

Crop species and compatible relatives.

| Crop Species | Compatible relatives |
| --- | --- |
| alfalfa | wild alfalfa |
| *Medicago sativa* | *Medicago sativa* |
| asparagus | wild asparagus |
| *Asparagus officinalis* | *Asparagus officinalis* |
| blueberry | wild blueberry |
| *Vaccinium angustifolium* | *Vaccinium angustofolium* |
| burmuda grass | wild burmuda grass |

TABLE 1-continued

Crop species and compatible relatives.

| Crop Species | Compatible relatives |
|---|---|
| *Cynodon dactylon* | *Cynodon dactylon* |
| carrot | wild carrot |
| *Daucus carota* | *Daucus carota* |
| celery | wild celery |
| *Apium graveolens* | *Apium graveolens* |
| chicory | wild chicory |
| *Chicorium intybus* | *Chicorium intybus* |
| clover | wild clover |
| *Trifolium* spp. | *Trifolium* spp. |
| corn | wild relatives of corn |
| *Zea mays* subsp. *mays* | *Zea mays* subsp. *mexicana* |
| | *Zea mays* subsp. *parviglumis* |
| | *Zea mays* subsp. *huehuetenangensis* |
| | *Zea diploperennis* |
| | *Zea perennis* |
| | *Zea luxurians* |
| cranberry | wild cranberry |
| *Vaccinium macrocarpon* | *Vaccinium macrocarpon* |
| foxtail millet | green foxtail |
| *Setaria italica* | *Setaria viridis* |
| lettuce | wild lettuce |
| *Lactuca sativa* | *Lactuca serriola* |
| oats | wild oats |
| *Avena sativa* | *Avena fatua* |
| oilseed rape, canola | wild radish |
| *Brassica napus* | *Raphanus raphanistrum* |
| | wild brassicas |
| | *Brassica napus* |
| | *Brassica campestris* |
| | *Brassica juncea* |
| quinoa | wild quinoa |
| *Chenopodium quinoa* | *Chenopodium berlandieri* |
| radish | wild radish |
| *Raphanus sativus* | *Raphanus raphanistrum* |
| rice | red rice* |
| *Oryza sativa* | *Oryza sativa* |
| | wild rice* |
| | *Porteresia coarctata* |
| tobacco | tobacco escaped from cultivation |
| *Nicotiana tabacum* | *Nicotiana tabacum* |
| sorghum | Johnsongrass |
| *Sorghum bicolor* | *Sorghum halapense* |
| squash | wild squash |
| *Cucurbita pepo* | *Cucurbita texana* |
| strawberry | wild strawberry |
| *Fragaria X ananassa* | *Fragaria virginiana* |
| sugar beets | wild beets |
| *Beta vulgaris* | *Beta vulgaris* |
| sunflower | wild sunflower |
| *Helianthus annuus* | *Helianthus annuus* |
| walnut | California walnut |
| *Juglans regia* | *Juglans hindsii* |
| wheat | jointed goatgrass* |
| *Triticum aestivum* | *Aegilops cylindrical* |
| | wheat grass* |
| | *Lophopyrum elongatum* |

The wild relative SOS1 polynucleotide is identified by using probes or polynucleotide sequences from SEQ ID NO: 1 to screen polynucleotide libraries or databases of wild relative genomic or cDNA. The wild relative's SOS1 polynucleotide has at least 50% homology to SEQ ID NO: 1, and confers an improvement in salt tolerance when transformed into its counterpart domesticated plant. Also included are functional fragments of the wild relative's SOS1 polynucleotide, which are at least 300 nucleotides in length, and which confer improved salt tolerance on the counterpart transformed domesticated plant.

The subject invention also extends to a method of improving salt tolerance of domesticated plants by transforming with the wild relative's SOS1 polynucleotide or functional fragments thereof. These methods can be carried out with wild relatives of corn, rice, cotton, soybean, wheat and alfalfa.

Further, the subject invention encompasses the wild relative's SOS1 polynucleotide identified by the foregoing methods, and to domesticated plants that have been transformed with wild relative SOS1 to improve salt tolerance.

All references cited herein are incorporated by reference in their entirety.

DETAILED DESCRIPTION OF THE INVENTION

Unless otherwise defined, all technical and scientific terms used herein have the same meaning as commonly understood by one of ordinary skill in the art of molecular biology. Although methods and materials similar or equivalent to those described herein can be used in the practice or testing of the present invention, suitable methods and materials are described herein. In case of conflict, the present specification, including definitions, will control. In addition, the materials, methods, and examples are illustrative only and are not intended to be limiting.

Reference is made to standard textbooks of molecular biology that contain definitions and methods and means for carrying out basic techniques, encompassed by the present invention. See, for example, Maniatis et al., Molecular Cloning: A Laboratory Manual, Cold Spring Harbor Laboratory Press, New York (1982) and Sambrook and Russell, Molecular Cloning: A Laboratory Manual, Cold Spring Harbor Laboratory Press, New York, 3$^{rd}$ Edtion (2001); Methods in Plant Molecular Biology, Maliga et al, Eds., Cold Spring Harbor Laboratory Press, New York (1995); *Arabidopsis*, Meyerowitz et al, Eds., Cold Spring Harbor Laboratory Press, New York (1994), Ausubel, et al., Current Protocols in Molecular Biology, Eds., Greene Publishing and Wiley-Interscience, New York (2000) and the various references cited therein.

The subject TSOS1 or salt cress SOS1 gene and its corresponding polypeptide provide a significant opportunity and advancement in agricultural genetic engineering due to the superior salt tolerance conferred by the SOS1 gene of *Thellungiella halophyte* as compared to the SOS1 gene of *Arabidopsis*. The discovery of the SOS1 gene provides methods for managing problems associated with increased salinity resulting from long-term irrigation, and methods for utilization of marginal agricultural areas and saltier irrigation water.

As discussed herein, the invention comprises the SOS1 gene of SEQ ID NO: 1, the polypeptide of SEQ ID NO: 3, and related polynucleotides and polypeptides that confer on a transformed plant cell or plant, a degree of salt tolerance that is improved relative to the salt tolerance exhibited by the untransformed plant cell or plant. Preferably, the improvement in salt tolerance relative to the untransformed plant or cell is at least 10%, 25% or more. Alternatively, the salt tolerance conferred by the homologous polynucleotide or polypeptide to the transformed plant or plant cell is substantially the same as that which is obtained with TSOS1 of SEQ ID NO: 1 and/or the polypeptide of SEQ. ID NO: 3.

Related molecules containing the subject polynucleotides are also included within the scope of the invention. Thus, cassettes comprising the polynucleotides and a heterologous promoter are included. Also, vectors comprising the polynucleotides and/or cassettes are within the scope of the invention. Further, host cells or plant cells, and transgenic plants are considered to be within the scope of the invention.

Cassettes and vectors can be synthesized using methods known in the art, and can be transformed into plant cells and plants using methods known in the art.

A polynucleotide that falls within the scope of the present claims can be identified by: (a) identifying a polynucleotide in a nucleic acid sample or in a database that: (i) has at least 85% homology to SEQ ID NO: 1; (ii) has at least 85% homology to a polynucleotide that encodes SEQ ID NO.:3, or (iii) that encodes a homologous polypeptide having at least 84% homology to the polypeptide of SEQ ID NO: 3; (b) expressing the polynucleotide of (a) in a cell or transgenic plant; and (c) determining whether the expressed polypeptide has Na+/H+ transporter activity.

The subject method also comprises a method for identifying homologous or orthologous SOS1 polynucleotides in plants that are wild relatives of domesticated plant species. In this context, a "domesticated plant" is any plant that has been cultivated by humans as a crop. For example, domesticated plants include corn, rice, soybean, cotton, alfalfa, wheat and the like, grown for human or animal consumption. It also includes flowering or other decorative plants grown for aesthetic or landscaping purposes. "Wild relatives" of domesticated plants are those plants that are wild ancestors of, or otherwise related, to the domesticated plants. Wild relatives of domesticated plants are known to persons of skill in the art. For example, teosinte is a wild relative and ancestor of domesticated corn. Wild relatives useful in the subject invention are those which exhibit greater salt tolerance than that exhibited by the domesticated plant.

To identify a homologous SOS1 polynucleotide in a wild, salt tolerant relative, a polynucleotide probe of at least 20 nucleotides of SEQ ID NO: 1 is used to screen mRNA transcripts, cDNA or genomic DNA from the wild, salt tolerant relative of the domesticated plant. In the alternative, the sequence of SEQ ID NO: 1, or a polynucleotide sequence of at least 20 nucleotides thereof, is used to "blast" a database containing genomic, cDNA or mRNA transcript sequences of the wild, salt tolerant relative, to identify the homologous SOS1 polynucleotide in the wild, salt tolerant relative. In a preferred embodiment, the homologous SOS1 polynucleotide has at least 50% homology to SEQ ID NO: 1. It is increasingly preferred that the minimum homology of the wild relative's SOS1 polynucleotide be 60%, 65%, 70%, 75%, 80%, 85%, 90%, 95% or 99%, when compared to SEQ ID NO: 1.

Next, the wild relative's homologous SOS1 polynucleotide or a functional fragment thereof is transformed into the domesticated plant using methods known in the art. The transformed domesticated plant is examined to determine whether it exhibits salt tolerance that is improved relative to the salt tolerance of the untransformed domesticated plant. A wild relative's homologous SOS1 polynucleotide that improves salt tolerance of a domesticated plant is considered to fall within the scope of the invention.

A "functional fragment" of the wild relative's SOS1 polynucleotide has a minimum length of at least 300 nucleotides, and with increasing preference, a minimum length selected from the group consisting of 600, 900, 1200, 1500, 1800, 2100, 2400, 2700, 3000, and 3300 nucleotides. The functional fragment retains the ability to confer salt tolerance on the transformed domesticated plant that is improved relative to the untransformed domesticated plant The subject invention also comprises a method for improving the salt tolerance of the domesticated plant. This is accomplished by identifying the wild relative's homologous SOS1 polynucleotide or functional fragment thereof, as discussed above, and transforming the wild relative's SOS1 polynucleotide or functional fragment into the domesticated plant, to produce a transformed domesticated plant with improved salt tolerance.

The foregoing methods of identifying SOS1 polynucleotides in wild, salt tolerant relatives, and using the SOS1 polynucleotides to enhance salt tolerance of domesticated species, can be carried out with wild relatives of corn, rice, cotton, soybean, wheat and alfalfa.

Example 2 exemplifies the foregoing methods. Salt cress is considered a wild relative of *Arabidopsis* Columbia. The *Arabidopsis* SOS1 gene was used to identify homologous salt cress SOS1 gene of SEQ ID NO: 1. The polynucleotide of SEQ ID NO: 1 was then used to transform the Columbia plants. As is demonstrated in Example 2, the transformed Columbia plants exhibit improved salt tolerance relative to the untransformed control Columbia plants. In fact, the Columbia plants transformed with salt cress SEQ ID NO: 1 polynucleotide was shown to have substantially greater salt tolerance as compared to the Columbia plants transformed with the *Arabidopsis* SOS1 gene, regardless of concentration of the NaCl solution.

The subject invention also extends to the wild relative's SOS1 polynucleotide which has been found by the foregoing methods to improve salt tolerance of the domesticated plant. The wild relative's domesticated relation can be corn, rice, cotton, soybean, wheat, alfalfa or the like.

The subject invention also extends to domesticated plants with improved salt tolerance obtained by transforming the plant with its wild relative's SOS1 polynucleotide. Again, such transformed domesticated plants can include corn, rice, cotton, soybean, wheat, alfalfa and the like.

Provided below are definitions of terms used herein:

"Enhancement" of a protein means increasing the intracellular activity of one or more proteins/enzymes in a plant cell and/or plant which are encoded by the corresponding DNA. Enhancement can be achieved with the aid of various manipulations of the cell. In order to achieve enhancement, particularly over-expression, the number of copies of the corresponding gene can be increased, a strong promoter can be used, or the promoter- and regulation region or the ribosome binding site which is situated upstream of the structural gene can be mutated. Expression cassettes which are incorporated upstream of the structural gene act in the same manner. In addition, it is possible to increase expression by employing inducible promoters. A gene can also be used which encodes a corresponding protein/enzyme with a high activity. Expression can also be improved by measures for extending the life of the mRNA. Furthermore, protein/enzyme activity as a whole is increased by preventing the degradation of the protein/enzyme. Moreover, these measures can optionally be combined in any desired manner. These and other methods for altering gene activity in a plant are known as described, for example, in Methods in Plant Molecular Biology, Maliga et al, Eds., Cold Spring Harbor Laboratory Press, New York (1995).

A gene can also be used which encodes a corresponding or variant protein/enzyme with a high activity. Preferably the corresponding protein/enzyme has a greater activity than the native form of the protein/enzyme, more preferably at least in the range of 5, 10, 25% or 50% more activity, most preferably more than twice the activity of the native or wild type enzyme.

"Fragment" refers to a portion of the polynucleotide sequence of SEQ ID NO:1 or homologs or degenerate variants thereof, or a portion of the polypeptide sequence of SEQ ID NO: 3. In the case of a polynucleotide sequence, the fragment is at least 300 nucleotides in length and encodes a polypeptide that has Na+/H+ transporter activity. The polynucleotide fragment, with increasing preference, has a minimum length of 600, 900, 1200, 1500, 1800, 2100, 2400, 2700, 3000 or 3300. In the case of a polypeptide sequence, the fragment is at least 100 amino acids in length and has Na+/H+ transporter activity. The polypeptide fragment, with increasing preference, has a minimum length of 200, 300, 400, 500, 600, 700, 800, 900, 1000 or 1100.

The SOS1 protein contains C-terminal and transmembrane N-terminal regions. The C-terminal region (about 100 amino acids) is cytosolic and undergoes phosphorylation reactions, while the N-terminal transmembrane region mediates Na+/H+ transport. This structure is similar to that reported for *Arabidopsis* SOS1 protein (Shi et al. (2000) PNAS 97:6896). Correlation of the subject SOS1 protein to the *Arabidopsis* SOS1 protein and other Na+/H+ antiporters reveals amino acids critical for function, and which should not be substituted (or only conservatively substituted) in functional homologs of the subject invention. Functional fragments of the subject invention can be selected according to information available from such comparative studies.

A "homologous" polynucleotide refers to a polynucleotide sequence that has, as compared to the polynucleotide sequences of the invention, at least 85% homology, and with increasing preference, a minimum homology percentage increasing incrementally by 1%, i.e., 86%, 87%, etc., up to and including 99%. According to the invention, a "homologous" protein is to be understood to comprise polypeptides which contain an amino acid sequence having at least 84% homology to the SOS1 polypeptide of SEQ ID NO: 3, and with increasing preference, a minimum homology percentage increasing incrementally by 1%, i.e., 85%, 86%, etc. up to and including 99%.

Homology, sequence similarity or sequence identity of nucleotide or amino acid sequences may be determined conventionally by using known software or computer programs such as the BestFit or Gap pairwise comparison programs (GCG Wisconsin Package, Genetics Computer Group, 575 Science Drive, Madison, Wis. 53711). BestFit uses the local homology algorithm of Smith and Waterman, Advances in Applied Mathematics 2: 482-489 (1981), to find the best segment of identity or similarity between two sequences. Gap performs global alignments: all of one sequence with all of another similar sequence using the method of Needleman and Wunsch, J. Mol. Biol. 48:443-453 (1970). When using a sequence alignment program such as BestFit, to determine the degree of sequence homology, similarity or identity, the default setting may be used, or an appropriate scoring matrix may be selected to optimize identity, similarity or homology scores. Similarly, when using a program such as BestFit to determine sequence identity, similarity or homology between two different amino acid sequences, the default settings may be used, or an appropriate scoring matrix, such as blosum45 or blosum80, may be selected to optimize identity, similarity or homology scores.

"Increased salt tolerance" means that the plant cell or plant exhibits increased resistance to or tolerance of elevated salinity in the water and/or soil. This is manifested by phenotypic characteristics known to the person skilled in the art including longer life span and apparent normal growth and function of the plant even during elevated salinity. Salt tolerance is measured by methods known in the art such as those described in Inan et al. (July 2004) Plant Physiol. 135:1718, including without limitation, NaCl shock exposure or gradual increase NaCl concentration. An example of NaCl shock exposure is exposure of 3-week-old seedlings to irrigation water of 500 mM NaCl every other day. An example of gradual increase in NaCl exposure is exposure of 3 week-old seedlings to irrigation water with 75 mM NaCl for 5 days, followed by increases to 150, 200, 300, 400 and 500 mM on days 5, 9, 16, 22 and 26 (Inan et al. (2004), supra). Root growth and shoot growth or other parameters such as seed production can be measured as an indication of salt tolerance.

"Introduction of the polynucleotide into the plant" refers to any of a number of methods known to the skilled artisan for introduction of heterologous polynucleotide into a plant cell or plant. Such methods are described without limitation in the Examples.

"Isolated" means separated from its natural environment.

"Plant" refers to whole plants, plant organs (e.g., leaves, stems, roots, etc.), seeds and plant cells and progeny of same. The class of plants which can be used in the methods of the invention is generally as broad as the class of higher plants amenable to transformation techniques, including both monocotyledonous and dicotyledonous plants. Preferred plants include rice, corn, wheat, cotton, peanut, oat, tomato, alfalfa, canola, sunflower and soybean, and all other ornamental and forestry plants.

"Polynucleotide" refers in general to polyribonucleotides and polydeoxyribonucleotides, and can denote and unmodified RNA or DNA or a modified RNA or DNA.

"Polypeptides" means peptides or proteins which contain two or more amino acids which are bound via peptide bonds.

"Polypeptides that have Na+/H+ transporter activity" refers to polypeptides or proteins that confer salt tolerance on a transformed plant cell or plant that is improved relative to the untransformed plant cell or plant.

"Polypeptides that substantially retain TSOS1 Na+/H+ transporter activity" refers to polypeptides or proteins that have at least 84% homology to SEQ ID NO: 3, and which confer salt tolerance on a plant cell or plant that is substantially the same as that provided by the TSOS1 polypeptide of SEQ ID NO: 3.

As mentioned above, salt tolerance can be measured by methods known in the art such as those described in Inan et al. (July 2004) Plant Physiol. 135:1718, including without limitation, growth of roots or shoots during and following NaCl shock exposure or a gradual increase in NaCl concentration. Salt tolerance conferred by a homologous polynucleotide or polypeptide is "substantially the same" as that provided by the SOS1 polypeptide of SEQ ID NO: 3, if it provide at least 80% or 90% of the salt tolerance provided by the TSOS1 of SEQ ID NO: 3 in the same plant cell or plant under the same experimental conditions. The salt tolerance that is conferred by the homologous polypeptide in question can be the result of expression or overexpression of a single or multiple corresponding polynucleotides.

"Stringent conditions" or "stringent hybridization conditions" includes reference to conditions under which a polynucleotide will hybridize to its target sequence, to a detectably greater degree than other sequences (e.g., at least 2-fold over background). Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing).

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° Celsius for short probes (e.g., 10 to 50 nucleotides) and at least about 60° Celsius for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37 degrees Celsius, and a wash in 1× to 2×SSC (20×SSC=3.0 M NaCl/0.3 M trisodium citrate) at 50 to 55 degrees Celsius. Exemplary moderate stringency conditions include hybridization in 40 to 45% formamide, 1 M NaCl, 1% SDS at 37 degrees Celsius, and a wash in 0.5× to 1×SSC at 55 to 60 degrees Celsius. Exemplary high stringency conditions include hybridization in 50% formamide, 1 M NaCl, 1% SDS at 37 degrees Celsius, and a wash in 0.1×SSC at 60 to 65 degrees Celsius.

Specificity is typically the function of post-hybridization washes, the critical factors being the ionic strength and temperature of the final wash solution. For DNA—DNA hybrids, the Tm can be approximated from the equation of Meinkoth and Wahl, Anal. Biochem., 138:267-284 (1984): Tm=81.5oC.+16.6 (log M)+0.41 (% GC)–0.61 (% form)–500/L; where M is the molarity of monovalent cations, % GC is the percentage of guanosine and cytosine nucleotides in the DNA, % form is the percentage of formamide in the hybridization solution, and L is the length of the hybrid in base pairs. The Tm is the temperature (under defined ionic strength and pH) at which 50% of a complementary target sequence hybridizes to a perfectly matched probe. Tm is reduced by about 1 degree Celsius for each 1% of mismatching; thus, Tm, hybridization and/or wash conditions can be adjusted to hybridize to sequences of the desired identity. For example, if sequences with approximately 90% identity are sought, the Tm can be decreased 10 degrees Celsius. Generally, stringent conditions are selected to be about 5 degrees Celsius lower than the thermal melting point (Tm) for the specific sequence and its complement at a defined ionic strength and pH. However, severely stringent conditions can utilize a hybridization and/or wash at 1, 2, 3, or 4 degrees Celsius lower than the thermal melting point (Tm); moderately stringent conditions can utilize a hybridization and/or wash at 6, 7, 8, 9, or 10 degree Celsius lower than the thermal melting point (Tm); low stringency conditions can utilize a hybridization and/or wash at 11, 12, 13, 14, 15, or 20 degrees Celsius lower than the thermal melting point (Tm). Using the equation, hybridization and wash compositions, and desired Tm, those of ordinary skill will understand that variations in the stringency of hybridization and/or wash solutions are inherently described. If the desired degree of mismatching results in a Tm of less than 45 degrees Celsius (aqueous solution) or 32 degrees Celsius (formamide solution) it is preferred to increase the SSC concentration so that a higher temperature can be used. An extensive guide to the hybridization of nucleic acids is found in Current Protocols in Molecular Biology, Ausubel, et al., Eds., Greene Publishing and Wiley-Interscience, New York (2000).

EXAMPLES

Example 1

Plant Transformation Methods

A DNA segment identified in this disclosure is isolated, and combined with at least a promoter functional in a plant cell to provide a recombinant expression cassette. An expression cassette comprising a recombinant DNA segment is subcloned into any standard expression vector by methods known to those of skill in the art. Suitable expression vectors include plasmids that autonomously replicate in prokaryotic and/or eukaryotic cells. The expression vector is introduced into prokaryotic or eukaryotic cells by currently available methods such as microprojectile bombardment, tungsten whiskers, and liposomes. The vector is introduced into prokaryotic cells such as *E. coli* or *Agrobacterium*. Transformed cells are selected typically by using a selectable screener marker encoded on the expression vector. A method to generate transgenic monocot plants is described in U.S. Pat. No. 6,281,411, the disclosure of which is herein incorporated by reference.

The expression vector or cassette is introduced into plant cells that include both monocot and dicot plants. Plant cells, or tissue, or organs useful for transformation include flowers, callus, immature embryos, meristematic tissue, gametic tissue, or cultured suspension cells. Other recombinant DNA molecules encoding proteins that enhance plant transformation may also be introduced. The transformed plant cell is regenerated into a plant and the plant is tested for its ability to grow or thrive under stress conditions, such a high salinity, reduced water availability, and adverse temperatures. Depending on the type of plant, the level of gene expression, and the activity of the protein encoded by the recombinant DNA segment, introduction of the recombinant DNA into the plant confers the phenotype of tolerance or resistance to the stress conditions to the plant.

The introduced recombinant DNA segment is expressed in the transformed plant cells and stably transmitted, somatically and sexually, to the subsequent cells produced. The vector is capable of introducing, maintaining, and expressing a recombinant DNA segment in plant cells, wherein the recombinant DNA is obtained from a variety of sources, including to plants, animals, bacteria, fungi, yeast, or virus. Additionally, the vector is introduced into a wide variety of plant cells.

Introduction and expression of foreign genes in dicotyledonous plants such as *Arabidopsis*, tobacco, potato, and alfalfa has been accomplished by using the T-DNA of the tumor inducing (Ti) plasmid of *Agrobacterium tumefaciens*. Through recombinant DNA techniques, a wide variety of foreign DNAs can be inserted into the T-DNA in *Agrobacterium*. Following infection by the bacterium containing the recombinant Ti plasmid, the foreign DNA is inserted into the host plant chromosomes, thus producing a genetically engineered cell and then a genetically engineered plant. Another approach is to introduce root-inducing (Ri) plasmids as gene vectors. Additionally, using the Ti plasmid as a model system, it may be possible to artificially construct transformation vectors for monocot plants. Ti plasmids may also be introduced into monocots by artificial methods such as microinjection, or fusion between monocot protoplasts and bacterial spheroplasts containing the T-region, which can then be integrated into the plant nuclear DNA. The selectable marker and heterologous gene expression cassettes described herein may be placed in a suitable expression vector designed for operation in plants. Suitable vectors are describe in U.S. Pat. Nos. 5,888,789 and 5,889,189, the disclosures of which are herein incorporated by reference.

Transformation of plant cells with recombinant DNA segments may also be accomplished by introducing a recombinant DNA into other nucleic acid molecules that can transfer the inserted DNA into a plant genome (i.e., plant pathogens such as DNA viruses like CaMV or gemini viruses, RNA viruses, and viroids); DNA molecules derived from unstable plant genome components like extrachromosomal DNA elements in organelles (i.e., chloroplasts or mitochondria) or nuclear-encoded controlling elements; DNA molecules from stable plant genome components (i.e., origins of replication and other DNA sequences which allow introduced DNA to integrate into the organellar or nuclear genomes and to replicate normally, to autonomously replicate, to segregate normally during cell division and sexual reproduction of the plant and to be inherited in succeeding generations of plants) or transposons.

A recombinant DNA may be delivered into plant cells or tissues directly by microorganisms with infectious plasmids, infectious viruses, the use of lipsomes, microinjection by mechanical or laser beam methods, by whole chromosomes or chromosome fragments, electroporation, and microprojectile bombardment. For example, callus cells or any other suitable tissue derived from the members of a desired plant species are transformed with an expression cassette that includes at least the recombinant DNA segment of interest, a selectable marker, and a suitable promoter using a variety of standard techniques (i.e., electroporation, *Agrobacterium*, protoplast fusion, or microparticle bombardment). A suitable transcription regulatory region (promoter) includes a plant promoter whose transcription is regulated in a response to various stress responses such as drought, salinity, and high temperature.

Suitable promoters include plant stress inducible promoter, viral coat protein promoter, a tissue-specific promoter, a monocot promoter, a ubiquitin promoter, a CaMV 35S promoter, a CaMV 19S promoter, a nos promoter, and Adh promoter, a sucrose synthase promoter, a tubulin promoter, a napin promoter, an actin promoter, a cab promoter, a PEPCase promoter, a 7S-alpha-conglycinin promoter, and R gene complex promoter, a tomato E8 promoter, a patatin promoter, a mannopine synthase promoter, a soybean seed protein glycinin promoter, a soybean vegetative storage protein promoter, a bacteriophage SP6 promoter, a bacteriophage T3 promoter, a bacteriophage T7 promoter, a PM promoter, a root-cell promoter, an ABA-inducible promoter, a turgor-inducible promoter, and any other stress-inducible promoters. Stress inducible promoters are particularly helpful. Exemplary transiently activated stress-inducible plant promoters are described in U.S. Pat. No. 6,414,221, the disclosure of which is herein incorporated by reference.

Example 2

Transformation of *Arabidopsis* with Salt Cress and *Arabidopsis* SOS1 Genes

*Arabidopsis* plants (Columbia) were grown in the greenhouse for 3 weeks in normal nutrient solution (Zhu et al. (2005) PNAS 102:9966) and then watered for ten days with the nutrient solution containing NaCl in concentrations indicated below. After 10 days, plants were re-watered with nutrient solution without any NaCl and the percent surviving plants were counted after two weeks. One hundred and fifty plants of each treatment and genotype were used in the experiment. Overexpression of SOS1-A and SOS1-SC salt cress was determined by RT-PCR and Northern blot analysis before and after salt treatment. Both SOS1-A and SOS1-SC plants accumulated 4 to 20 times more SOS1 transcript than control Columbia plants in three replicated experiments.

TABLE 2

Percent survival at various sodium chloride concentrations.

| | NaCl | | | |
|---|---|---|---|---|
| | 0 mM | 100 mM | 200 mM | 300 mM |
| | | % Survival | | |
| Control | 100 | 50 | 3 | 0 |
| SOS1 (SOS1-A) *Arabidopsis* | 100 | 65 | 40 | 10 |
| SOS1 (SOS1-SC) Salt Cress | 100 | 95 | 80 | 50 |

The foregoing results indicate that the salt cress SOS1 gene is superior to the SOS1 gene of *Arabidopsis* in conferring salt tolerance to transformed *Arabidopsis* Columbia plants.

These results are consistent with the report of Vera-Estrella et al. (2005) Plant Physiol. Preview, published after the priority date of the subject application. Vera-Estrella et al. describe how expression of SOS1 protein increases in salt cress leaves and roots after treatment of the plants with either 200 or 400 mM NaCl, indicating that the stress response even in salt cress is mediated (at least in part) by the SOS1 gene and polynucleotide.

The foregoing examples are intended to be illustrative and not exclusive.

The invention claimed is:

1. An isolated polynucleotide having a sequence selected from the group consisting of: a) the nucleic acid sequence of SEQ ID NO: 1; b) a nucleic acid sequence having at least 95% sequence identity to the SEQ ID NO: 1, and encoding a polypeptide that has Na+/H+ transporter activity; and c) a nucleic acid sequence encoding the polypeptide of SEQ ID NO: 3, or encoding a polypeptide having at least 95% sequence identity to the polypeptide of SEQ ID NO: 3, and which has Na+/H+ transporter activity.

2. A cassette comprising a heterologous promoter operably linked to the polynucleotide of claim 1.

3. The cassette of claim 2, wherein the promoter is an inducible promoter.

4. A vector comprising the cassette of claim 2.

5. A host cell comprising the cassette of claim 2 and wherein the host cell expresses the polynucleotide.

6. A plant cell comprising the cassette of claim 2 and wherein the plant cell expresses the polynucleotide.

7. A plant organ or seed comprising the cassette of claim 2 and wherein said plant organ or seed expresses the polynucleotide.

8. A transgenic plant comprising the cassette of claim 2 and wherein the transgenic plant expresses the polynucleotide.

9. A progeny of the transgenic plant of claim 8, wherein the progeny comprises said polynucleotide.

10. The transgenic plant of claim 8 selected from the group consisting of *Arabidopsis thaliana*, wheat, corn, peanut, cotton, oat, tomato, rice, alfalfa, canola, sunflower and soybean plants.

11. A method of making a transgenic plant with increased salt tolerance as compared to the plant's untransformed state, comprising introducing the polynucleotide of claim 1 into said plant and expressing said polynucleotide that confers salt tolerance.

12. An isolated polynucleotide having a nucleic acid sequence which is fully complementary to the isolated polynucleotide of claim 1.

* * * * *